United States Patent [19]
Pfeiffer

[11] Patent Number: 5,878,744
[45] Date of Patent: Mar. 9, 1999

[54] VENTILATOR SYSTEM AND METHOD OF OPERATING A VENTILATING SYSTEM

[75] Inventor: Georg Pfeiffer, Djursholm, Sweden

[73] Assignee: Siemens Elema AB, Solna, Sweden

[21] Appl. No.: 898,257

[22] Filed: Jul. 22, 1997

[30] Foreign Application Priority Data

Aug. 2, 1996 [SE] Sweden .................................. 9602913

[51] Int. Cl.$^6$ ................................................ A61M 15/00
[52] U.S. Cl. .............................. 128/204.23; 128/204.22; 128/205.23
[58] Field of Search .................... 128/204.23, 200.24, 128/204.21, 204.22, 203.12, 205.23

[56] References Cited

U.S. PATENT DOCUMENTS

| | | | |
|---|---|---|---|
| 4,393,869 | 7/1983 | Boyarsky et al. . | |
| 5,303,698 | 4/1994 | Tobia et al. . | |
| 5,720,277 | 2/1998 | Olsson et al. ....................... | 128/204.22 |
| 5,720,278 | 2/1998 | Lachmann et al. ................. | 128/204.23 |
| 5,743,253 | 2/1998 | Castor et al. ....................... | 128/200.24 |

FOREIGN PATENT DOCUMENTS

| | | |
|---|---|---|
| 0 723 785 | 7/1996 | European Pat. Off. . |
| WO 95/16484 | 6/1995 | WIPO . |

OTHER PUBLICATIONS

Operational Manual for Servo Ventilator 300, Manufactured by Siemens–Elema AB, pp. 94–98 (1993).

Brochure for Option 30/40 for the Puritan Bennett 7200 Series Microprocessor, Mar. 1986.

*Primary Examiner*—John G. Weiss
*Assistant Examiner*—Charles W. Anderson
*Attorney, Agent, or Firm*—Hill & Simpson

[57] ABSTRACT

In a ventilator system and a method of operating the ventilator system, the ventilator system has a ventilator and a connection system for connecting the ventilator system to a patient. Parameters for a respiration gas pattern are set on the ventilator. Due to the influence of the connection system on the respiration gas pattern, the generation of the respiration gas pattern needs to be calibrated in order to ensure that the set respiratory gas pattern is delivered to the patient. In order to obtain calibration factors a test gas pulse is generated by an inspiration system before connecting the patient. Measurements of the test gas pulse are made with parameter meters at different locations in the connection system. The parameters for the test gas pulse, as well as the measured parameters are stored in different data sets. By synchronizing and subtracting measured parameter data sets from the set parameter data set, calibration factors are obtained.

13 Claims, 2 Drawing Sheets

VENTILATOR SYSTEM AND METHOD OF OPERATING A VENTILATING SYSTEM

BACKGROUND OF THE INVENTION

1. Field of the Invention

The present invention is directed to a method of operating a ventilator system, of the type having a ventilator and a connection system for, when connected to a patient, conveying gas to and from the patient.

The present invention is also directed to a ventilator system of the type having an inspiration section for generating an inspiratory respiratory gas pattern, a connection system for, when connected to a patient, conveying gas to and from the patient, an expiration section for generating an expiratory respiratory gas pattern, a measurement system for measuring respiratory gas pattern parameters at different sites in the ventilator system and a control unit for controlling the operation of the ventilator system based on set operational parameters and measured parameters.

2. Description of the Prior Art

In the past 50 years, the development of ventilator systems (which in as used herein means all respirator/ventilator systems as well as anaesthetic systems) has made rapid progress. From initially using simple mechanical piston systems to impose breathing gas on the patient at every piston stroke, today's ventilator systems can be controlled to supply a breathing gas to a patient according to a number of different operating modes, a physician then being able to select the operating mode deemed most suitable for the patient.

A ventilator system can be described as a ventilator with a connection system for connecting the ventilator to the patient. One known ventilator is the Servo Ventilator 300, Siemens-Elema AB, Solna, Sweden. This ventilator is equipped with a very fast and accurate gas regulation system. In practice, this means that a gas flow can be generated with an optional respiratory gas pattern, as used herein, the term respiratory gas pattern refers to pressure and flow characteristics over time. Pressure and flow in any given respiratory gas pattern can exhibit predefined variations over time.

Even if the regulatory system is capable of generating a gas flow which corresponds almost exactly to the target respiratory gas pattern, it is not certain that the gas flow received by the patient has the target respiratory gas pattern. This because of the interposed connection system, which influences the respiratory gas pattern.

The connection system can i.a. include tubes, humidifiers, dehumidifiers and bacterial filters. Flow resistance in gas lines and other components in the connection system influences the respiratory gas pattern in one way. The total volume taken up by the connection system influences the respiratory gas pattern in another way. This because gases are highly compressible. The influence to which the respiratory gas pattern is subjected by the connection system changes the pattern of gas flow with respect to delay and morphology (morphology here referring to variations in pressure and flow over time).

Attempts have previously been made to compensate, at least to some extent, for the influence of the connection system. For example, the operational manual for the aforementioned Servo Ventilator 300, AG 0593 3.5, Siemens-Elema AB, 1993, pp. 94–98, describes compensation for the connection system's compressible volume. Compensation in this case means that the physician must set a larger minute volume for the breathing gas to be supplied to the patient in order to ensure the delivery to the patient of the target minute volume. Here, the physician is forced to make the calculations required to achieve the necessary compensation. The calculation example on page 98 in the operational manual, meant for an adult patient, shows that minute volume has to be increased by 2.5 1/m when the target minute volume was 7.5 1/m. Compensation naturally varies from case to case. The need for compensation depends in particular on the configuration of the connection system. The calculation example, however, does provide an indication of the compensation needed for minute volume.

There are also other known ventilator systems offering compensation, either by a physician or by a programmed automatic function. The compensation mainly entails a determination of the connection system's compressible volume, for instance the Puritan Bennet, 7200 Series Microprocessor ventilator, option 30/40, part number 20522A, March 1986.

Determination of compressible volume, however, does not really indicate how a respiratory gas pattern is actually influenced and altered by the connection system. As noted above, respiratory gas pattern refers to pressure and flow variations over time. If the flowing gas is viewed as a gas column passing through the connection system, it will be realized that even simple compression of the gas column changes slopes of the non-constant parts of the column and, in particular, the pressure and flow variations over time. Thus, compressible volume does not indicate anything about, for instance, the way in which a target pressure increase the gas column is influenced on its way to the patient's respiratory system. Determining compensation for the connection system's compressible volume therefore does not supply sufficient information for the use in calculating compensation of the respiratory gas pattern. As already noted, the flow of gas is also delayed in the connection system. It may even be, that different parts of the connection system imposes different delays on the respiratory gas pattern.

In conjunction with both the diagnoses and treatment of disorders in the respiratory system (primarily the lungs) of a patient, determination of the lung's various mechanical parameters is desirable. Determination of resistance and compliance is especially important. Roughly speaking, compliance can be determined in ways similar to determinations of compressible volume in the connection system of the known ventilator systems. A particular problem, however, is that the connection system's influence on gas flow is not fully known in conventional ventilator systems, so determination of the lungs mechanical parameters is even more uncertain. Moreover, the properties of these mechanical parameters can also influence the respiratory gas pattern.

In conjunction with the development of increasingly more accurate and exact gas generating systems in the ventilator field, the ability to determine and take into account factors for which compensation previously could not be made is also more desirable.

By using complex mathematical methods, models representing the influence of each component in the connection system can be assumed and a model for the entire connection system can be calculated mathematically and used as an overall compensating model for the connection system. Such models, however, require that the transfer function for each component be verified not only for the component itself but also when interacting with other components in the connection system. Since components are manufactured by several manufacturers, each component from each manufacturer must be tested and verified as to its mathematical model. In practice, a physician must then program the ventilator system for each new configuration of the connection system.

Another possibility is to regard the entire connection system as an unknown transfer system, having an unknown transfer function. In an earlier Swedish patent application SE 9500275-4, corresponding to co-pending U.S. application Ser. No. 08/588,684 filed Jan. 16, 1996 ("METHOD AND APPARATUS FOR MAINTAINING A DEFINED RESPIRATORY GAS FLOW PATTERN TO A SUBJECT BY IDENTIFYING A TRANSFER FUNCTION OF THE CONNECTION SYSTEM," Castor et al.), assigned to the same assignee as the present application, such a system is described. A test gas pulse is generated by the ventilator and the resulting gas pulse responses are measured at different sites in the ventilator system. By using the resulting gas pulse response and the test gas pulse in mathematical methods of calculation, for instance Box Jenkins model structures or similar, a transfer function can be calculated for the entire connection system. This requires, however, the presence of fairly strong computer calculation capabilities.

SUMMARY OF THE INVENTION

An object of the present invention is to provide a method for obtaining information relating to the static and dynamic influence of a connection system of a ventilator system in a relatively easy manner without undertaking unnecessary calculations.

Another object of the invention is to provide a method for obtaining more relevant information regarding the properties of a respiratory system, when connected to the ventilator system.

Yet another object of the invention is to provide a ventilator system which in an easy manner can produce information relevant for the influence of the connection system.

The first object is achieved in accordance with the invention in a method including the steps of setting a number of operational parameters for a test gas pulse, storing the set operational parameters as a first dataset, delivering the test gas pulse, measuring parameters of a resulting gas pulse response, storing the measured parameters as at least one second dataset and forming at least one third dataset based on the first dataset and the second dataset, the third dataset containing information relating to the static and dynamic influence and/or properties of at least one flow path within the ventilator system.

In a straightforward embodiment, the measured parameters are measured at one specific site in the connection system and the two datasets represent the time dependent variation of pressure flow etc at two different sites in the ventilator system (one being the target pattern and the other the resulting pattern). The third dataset is formed based on the first and second dataset and contains the necessary information for determining how the connection system or at least a part of the connection system, (when the measurement site cannot measure the influence of the entire connection system), has influenced the generated test gas pulse. This information may be used to calibrate the generation of respiratory gas patterns, but may also be used for determining the resistance and compressible volume in the connection system (or the specific part of the connection system).

In a more complex embodiment, the measured parameters are measured at several sites. Both partial and total influences can then be determined in the same simplistic manner.

The measured parameters can be stored in several data sub-sets to the second dataset or directly as several datasets.

In a further version of the method, the data stored in the first and second datasets are synchronized before forming the third dataset. The synchronization can be performed by including a change in the composition of the gas in the test gas pulse, such as changing the concentration of $CO_2$ or $O_2$ or any other component gas. The change in composition can also be realized as a complete change of singular gases, for instance changing from $N_2O$ to pure $O_2$ or similar. The gas selected for the change depends on a number of factors, such as if the system is a straightforward ventilator system for providing air and oxygen, or a complex anaesthetic system.

In another version of the method the procedure is repeated after connection of a patient to the ventilator system. This results in a fourth dataset being obtained, which contains information of the patient's influence on the complete connection system. The patient-related parameters can then be determined and the generation of respiratory gas patterns can be compensated by the influence of the patient on the connection system, as well.

Another of the objects of the invention is achieved in a ventilator system having a control unit that controls the inspiration section to generate a test gas pulse based on set operational parameters for the test gas pulse. The control unit has a data storage and calculation system for storing the set operational parameters as the first dataset and for storing parameters measured by the measurement system as the second dataset. The data storage and calculation system form the third dataset based on the first dataset and the second dataset.

DESCRIPTION OF THE PREFERRED EMBODIMENTS

Figure 1:
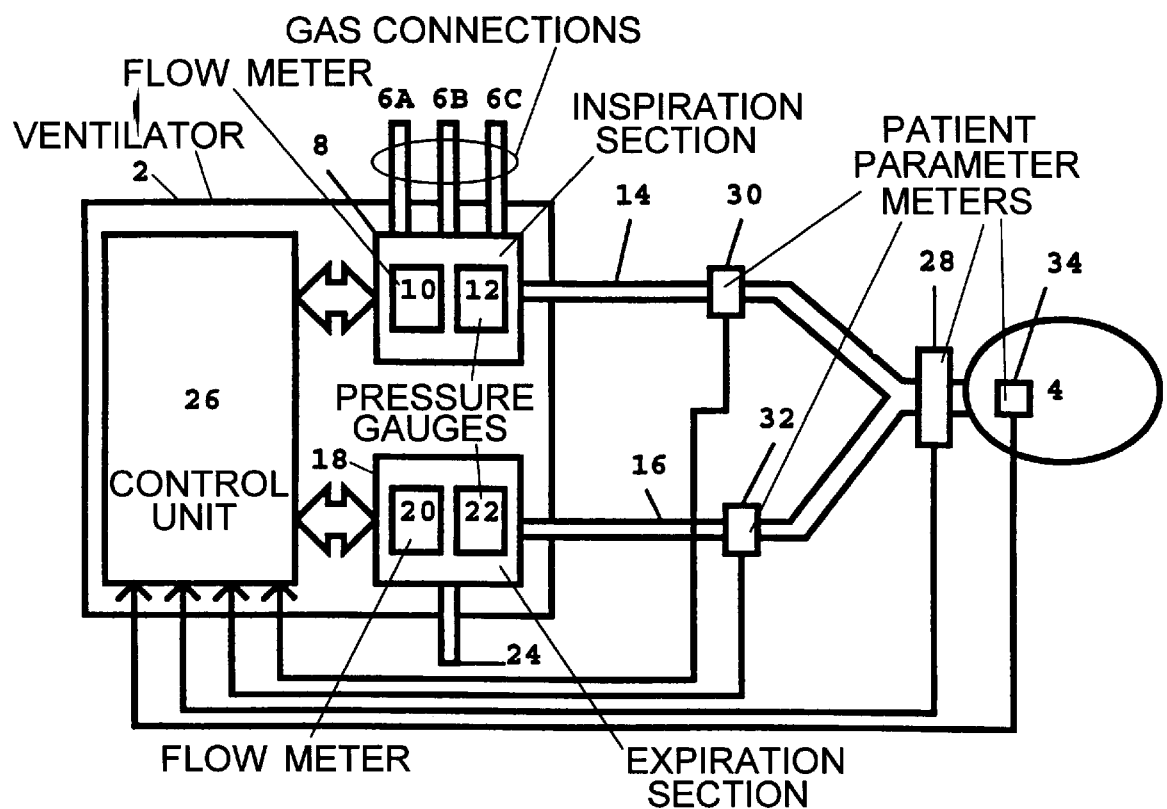
FIG. 1 shows a ventilator system according to the invention connected to a patient.

FIG. 1 shows a ventilator system according to the invention. The ventilator system includes a ventilator 2 connected to a patient 4 for supplying respiratory gas to and conveying respiratory gas from the patient 4. The ventilator 2 can be connected to external gas sources via a first gas connection 6A, a second gas connection 6B and a third gas connection 6C. Via the gas connections 6A–6C different gases can be supplied to the ventilator- 2. Air, oxygen, nitrous oxide and other gases can be supplied, depending on the purpose for supplying respiratory gas to the patient 4. The gases supplied to the ventilator 2 are led to an inspiration section 8 which includes control elements such as valves and a mixing chamber for controlling flow, pressure and composition (over time) of a respiratory gas. The control elements and their operation are well known. For instance the Servo Ventilator 300, described above, employs such control elements. The inspiration section 8 further includes a first flow meter 10 for measuring the flow generated by the inspiration section 8 and a first pressure gauge 12 for measuring the pressure generated by the inspiration section 8. The first flow meter 10 can have one flow sensor for the total flow or several flow sensors, one for each gas supplied. In the latter case the sum of the flow sensors represent the total flow measured by the first flow meter 10.

During normal operation, respiratory gas is conducted via an inspiration line 14 to the patient 4 for providing controlled or supported inspiration phases.

During expiration, respiratory gas is conveyed from the patient 4 via an expiration line 16 to an expiration section 18 in the ventilator 2. The expiration section 18 includes a valve (not shown) for controlling the expiration flow and also for controlling the pressure in the expiration line 16.

The expiration section 18 also includes a second flow meter 20 and a second pressure gauge 22 for measuring the flow and the pressure at the end of the expiration line 16.

After passing the expiration section 18, the expired gas is conducted via an expiration outlet 24 either to ambient atmosphere or to an evacuation system (not shown).

The operation of the ventilator 2 is controlled by a control unit 26 which can contain analog control systems or one or several microprocessors for controlling the inspiration section 8 and the expiration section 18.

Pressure, flow and/or composition of the respiratory gas can also be measured in a first patient parameter meter 28, connected near the patient 4. Further measurement meters can also be disposed at different sites in the inspiration line 14, such as a second patient parameter meter 30, in the expiration line 16, such as a third patient parameter meter 32, or even within the patient, such as a fourth patient parameter meter 34.

The ventilator 2, the patient parameter meters 28, 30, 32 and 34, the inspiration line 14 and the expiration line 16 in combination form a ventilator system, wherein the inspiration line 14 and the expiration line 16 constitute a connection system. The connection system usually also includes a humidifier a dehumidifier, a bacterial filter etc., (but these not shown).

Figure 2:
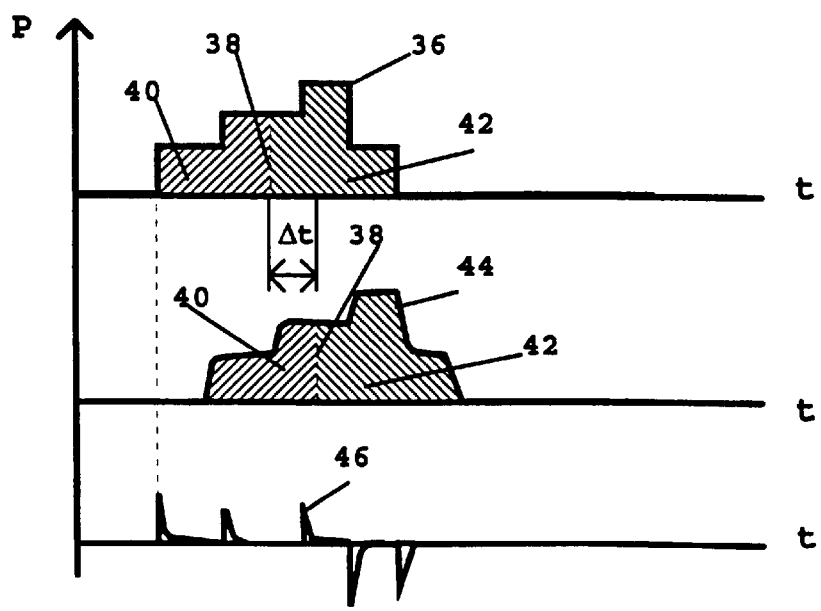
FIG. 2 shows a test gas pulse delivered by the ventilator system of FIG. 1, a resulting gas pulse response and a correction diagram.

The connection system will influence the respiratory gas pattern generated at the inspiration section 8. In particular, the respiratory gas pattern, set by a physician at the ventilator 2, will change before it reaches the patient 4. In order to compensate the generation of the respiratory gas pulse for this influence, thereby ensuring that the patient will receive the set respiratory gas pattern, measurements are made on a test gas pulse generated by the inspiration section 8 before the patient 4 is connected to the ventilator system. In FIG. 2 one test gas pulse is shown. The test gas pulse 36 has several pressure levels and is designed to include most of the pressure and flow characteristics which are present in the different modes intended to be used for a particular patient, or which are available for use with the ventilator system. Instead of using one test pulse, several test pulses, selected from different modes of operation can be used. It is also possible to use only one test pulse selected from one of the modes. Using a test gas pulse having several flow and pressure characteristics, however, provides for a faster and more accurate determination of the compensation which is required.

The test pulse 36 also includes a change in gas composition indicated at designation 38. The first part of the test pulse 36, indicated as area 40, therefore will have one gas composition and the second part of the test pulse 36, indicated as area 42, will have another gas composition. It should be noted, however, that a change in the composition of gas is not necessary for the method according to the invention, but it provides an accurate and easy locatable marker for later synchronization (as described below).

As the test pulse 36 is delivered, measurements will be made at one or several sites, as indicated by the patient parameter meters in FIG. 1. One resulting test pulse response 44 is shown in the diagram in FIG. 2. By identifying the certain point in time (designation 38) where the gas composition is changed, a time delay At for the connection system can be identified and the two curves 36 and 44 can be synchronized in order to obtain a calibration curve 46. The calibration curve 46 basically indicates how the generation of a respiration gas pulse with a specific pressure and flow pattern must be compensated in order to ensure that a specific gas pulse pattern, set by a physician, reaches the patient. The correction can be obtained by using the pressure step in the test pulse 36 that corresponds most accurately to the pressure step set by the physician and locating the corresponding portion of the correction curve 46.

In FIG. 2 the test gas pulse 36, response pulse 44 and calibration curve 46 are indicated as curves in a diagram. This has been done in order to visualize the method more clearly. In practice, it is more preferable to sample all information with a specific sample rate, for instance 50–200 Hz and to store the samples as datasets in a memory in the control unit 26. One dataset represents the test gas pulse and one or several datasets represent the measured information and calibration factors. The correction dataset can even be a look-up table, where the settings made by a physician for the respiration gas pattern to the patient are entered at the ventilator and are used as an entry code for the look-up table, thereby obtaining the relevant correction factor required for achieving the selected respiratory gas pattern as a read-out from the look-up table.

A correction dataset can be obtained by forming the difference between a dataset having set parameters for the test gas pulse and a dataset having measured parameters at the connection site for the patient. The difference is formed after the datasets have been synchronized by identifying the change in the composition of gas.

An alternative way of synchronizing the data (and determining the delay time) is to include and identify specific pressure and/or flow increases or decreases. It is also possible to use a complex test gas pulse or a series of test gas pulses and to use mathematical methods for matching the information (e.g. least square method or similar). The latter, however, requires more calculation power.

The obtained measurements also contain information such as resistance and compliance of the connection system (or measured parts of the connection system). By measuring at several sites, the connection system can be analyzed partially. This allows information of the influence of single elements within the connection system to be obtained.

As stated above, the test gas pulse 36 will be delivered before the patient 4 is connected to the connection system. The open end of the connection system, where the patient 4 will be connected, may either be blocked or connected to a simulated lung (dummy), for instance a gas bag or an artificial respiration system with predetermined characteristics. After the patient 4 is connected to the connection system a new test gas pulse or pulses may be supplied and new measurements be made. Based on the new measurements and the previous measurements (before connecting the patient 4) the influence caused by the patient 4 can also be determined, so that diagnostic information (such as resistance and compliance) can be obtained for the physician to use for further refining the following therapy to be given to the patient.

Figure 3:
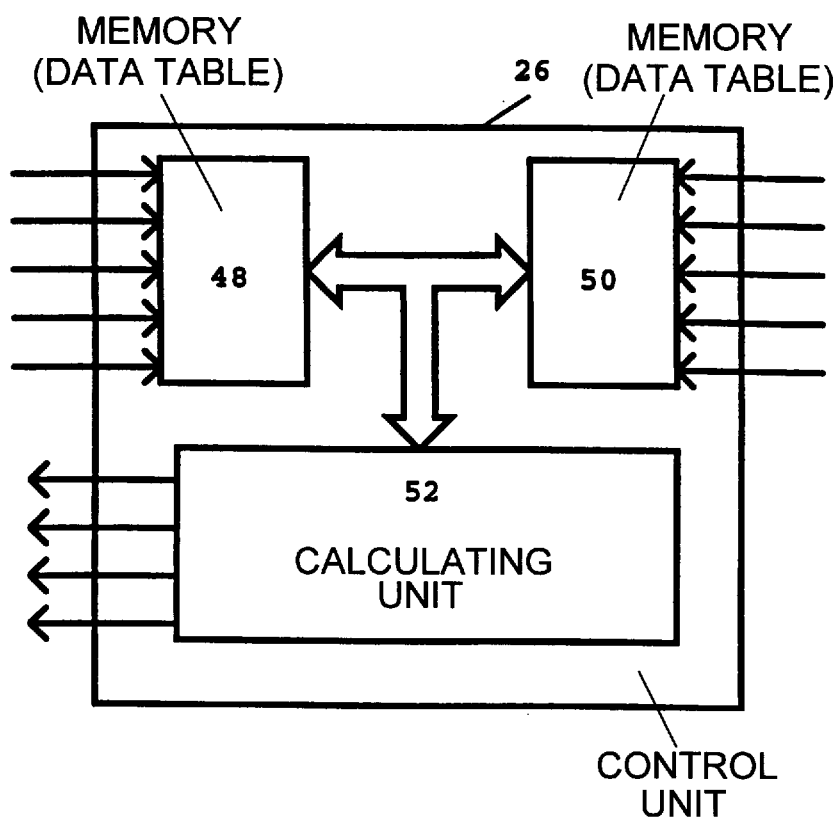
FIG. 3 shows details of an embodiment a control unit for the ventilator system of FIG. 1.

FIG. 3 shows a simple block diagram structure of the control unit 26, in which a first memory or data table 48 collects the set parameters for a respiration gas pattern or test gas pulse and a second memory or data table 50 collects the resulting measured parameters. The data from the two memories or data tables 48 and 50 are transferred to a calculating unit 52, wherein a subtraction of the two data tables is made after synchronization for obtaining the third data table or dataset. This third dataset includes the required calibration factors for the reference signal generator, or control system signals which control the inspiration section and the expiration section.

The present method may be used in a similar way for all kinds of respirator or ventilator systems, including anaesthetic systems.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating a ventilator system having a ventilator and a connection system for, when connected to a patient, conveying gas to and from that patient, said method comprising the steps of:

setting a plurality of operational parameters for a test gas pulse;

storing said operational parameters as a first dataset;

delivering a test gas pulse having said operational parameters to said connection system, and thereby producing a resulting gas pulse response;

measuring parameters of said resulting gas pulse response;

storing the measured parameters of said resulting gas pulse response as a second dataset; and forming a third dataset based on said first dataset and said second dataset comprising, for at least one flow path within said ventilator system, information selected from the group consisting of a static influence of said at least one flow path, a dynamic influence of said at least one flow path, and properties of said at least one flow path.

2. A method as claimed in claim 1 comprising the additional step of synchronizing said first dataset in said second dataset before forming said third dataset.

3. A method as claimed in claim 1 comprising the additional steps of:

including a change in a composition of gas in said test gas pulse;

identifying, in each of said first dataset and said second dataset, a point in time at which said change in the composition of gas in said test gas pulse occurs; and synchronizing said first dataset and said second dataset by causing the respective points in time of said change in said first dataset and in said second dataset to coincide.

4. A method as claimed in claim 1 wherein the step of forming said third dataset comprises subtracting said second dataset from said first dataset.

5. A method as claimed in claim 1 comprising the additional set of supplying a respiratory gas pattern from said ventilator system via said connection system having operation parameters dependent on said information in said third dataset.

6. A method as claimed in claim 5 comprising the additional steps of:

storing said third dataset as correction factors in a look-up table having said operational parameters of said respiratory gas pattern as an entry code; and supplying said operational parameters to said look-up table for obtaining a correction factor.

7. A method as claimed in claim 1 comprising the additional steps of:

connecting a patient to said ventilator system after forming said third dataset; and repeating the steps of setting said operational parameters for a test gas pulse, storing said first dataset, delivering said test gas pulse, measuring parameters of said resulting gas pulse response and storing the measured parameters of said resulting gas pulse response with said patient connected to said connection system, and obtaining a fourth dataset, said fourth dataset in combination with said first, second and third datasets comprising diagnostic information identifying properties of the respiratory system of said patient.

8. A method as claimed in claim 7 comprising the additional steps of:

forming a fifth dataset from said fourth dataset; and supplying a respiratory gas pattern to said patient from said ventilator system via said connection system having operational parameters adjusted dependent on said fifth dataset.

9. In a ventilator system including a ventilator and a connection system for, when connected to a patient, conveying gas to and from that patient, the improvement comprising:

means for setting a plurality of operational parameters for a test gas pulse;

means for storing said operational parameters as a first dataset; for delivering a test gas pulse having said operational parameters to said means connection system, and thereby producing a resulting gas pulse response;

means for measuring parameters of said resulting gas pulse response;

means for storing the measured parameters of said resulting gas pulse response as a second dataset; and means for forming a third dataset based on said first dataset and said second dataset comprising, for at least one flow path within said ventilator system, information selected from the group consisting of a static influence of said at least one flow path, a dynamic influence of said at least one flow path, and properties of said at least one flow path.

10. The improvement of claim 9 further comprising means for synchronizing said first dataset and said second dataset before forming said third dataset in said means for forming a third dataset.

11. The improvement of claim 9 further comprising:

means for including a change in a composition of gas in said test gas pulse;

means for identifying, in each of said first dataset and said second dataset, a point in time at which said change in the composition of gas in said test gas pulse occurs; and means for synchronizing said first dataset and said second dataset by causing the respective points in time of said change in said first dataset and in said second dataset to coincide.

12. The improvement of claim 9 wherein said means for forming said third dataset comprises means for subtracting said second dataset from said first dataset.

13. The improvement of claim 9 further comprising:

means for storing said third dataset as correction factors in a look-up table having said operational parameters of said respiratory gas pattern as an entry code; and means for supplying said operational parameters to said look-up table for obtaining a correction factor.

* * * * *